United States Patent
Laster

(10) Patent No.: US 9,649,427 B2
(45) Date of Patent: May 16, 2017

(54) SYSTEM AND METHOD FOR BLOOD FILTERING AND/OR TREATMENT

(71) Applicant: Clil Medical Ltd., Jerusalem (IL)

(72) Inventor: Morris Laster, Jerusalem (IL)

(73) Assignee: XEREM MEDICAL LTD., Tel-Aviv (IL)

( * ) Notice: Subject to any disclaimer, the term of this patent is extended or adjusted under 35 U.S.C. 154(b) by 234 days.

(21) Appl. No.: 14/368,537

(22) PCT Filed: Dec. 27, 2012

(86) PCT No.: PCT/IL2012/050558
§ 371 (c)(1),
(2) Date: Jun. 25, 2014

(87) PCT Pub. No.: WO2013/098823
PCT Pub. Date: Jul. 4, 2013

(65) Prior Publication Data
US 2014/0358060 A1    Dec. 4, 2014

Related U.S. Application Data

(60) Provisional application No. 61/580,685, filed on Dec. 28, 2011.

(51) Int. Cl.
*A61M 1/14* (2006.01)
*A61M 1/38* (2006.01)
(Continued)

(52) U.S. Cl.
CPC ............ *A61M 1/38* (2013.01); *A61M 1/1678* (2013.01); *A61M 1/34* (2013.01); *A61M 1/3639* (2013.01);
(Continued)

(58) Field of Classification Search
CPC ...... A61M 1/165; A61M 1/1678; A61M 1/34; A61M 1/3639; A61M 1/3655; A61M 1/38;
(Continued)

(56) References Cited

U.S. PATENT DOCUMENTS 3,815,605 A    6/1974   Schmidt et al.
3,949,428 A    4/1976   Cavendish et al.
(Continued)

FOREIGN PATENT DOCUMENTS

CN    102462871 A    5/2012
CN    203724186 U    7/2014
(Continued)

OTHER PUBLICATIONS

International Search Report and the Written Opinion Dated May 9, 2013 From the International Searching Authority Re. Application No. PCTIL2012/050558.
(Continued)

*Primary Examiner* — Jacqueline Stephens
*Assistant Examiner* — Benjamin Klein
(74) *Attorney, Agent, or Firm* — Clements Bernard Walker PLLC; Christopher L. Bernard; Lawrence A. Baratta, Jr.

(57) ABSTRACT

A system for filtering or treating blood of a subject is provided herein. The system includes a bone port for establishing fluid communication with a bone marrow of the bone and a return port for returning blood from the bone marrow to a circulation of the subject. The system further includes a blood treatment or filtering device interposed between the bone and return ports thereby establishing a mini-circulatory system.

24 Claims, 7 Drawing Sheets

(51) Int. Cl.
*A61M 1/34* (2006.01)
*A61M 1/16* (2006.01)
*A61M 1/36* (2006.01)
*A61M 5/165* (2006.01)
*A61M 39/02* (2006.01)

(52) U.S. Cl.
CPC .......... *A61M 1/3655* (2013.01); *A61M 5/165* (2013.01); *A61M 2005/1657* (2013.01); *A61M 2039/025* (2013.01); *A61M 2039/0264* (2013.01); *A61M 2039/0276* (2013.01); *A61M 2202/0021* (2013.01); *A61M 2202/0035* (2013.01); *A61M 2202/0042* (2013.01); *A61M 2202/0413* (2013.01); *A61M 2202/10* (2013.01); *A61M 2205/04* (2013.01); *A61M 2205/7563* (2013.01); *A61M 2210/005* (2013.01); *A61M 2210/02* (2013.01); *A61M 2210/1085* (2013.01)

(58) Field of Classification Search
CPC .... A61M 2005/1657; A61M 2039/025; A61M 2039/0264; A61M 2039/0276; A61M 2202/0021; A61M 2202/0035; A61M 2202/0042; A61M 2202/0413; A61M 2202/10; A61M 2205/04; A61M 2205/7563; A61M 2210/02; A61M 2210/10; A61M 2210/1085
See application file for complete search history.

(56) References Cited

U.S. PATENT DOCUMENTS

| | | |
|---|---|---|
| 4,772,261 A | 9/1988 | Von Hoff et al. |
| 4,936,851 A | 6/1990 | Fox et al. |
| 5,120,312 A | 6/1992 | Wigness et al. |
| 5,192,282 A | 3/1993 | Draenert |
| 5,372,583 A | 12/1994 | Roberts et al. |
| 5,397,354 A | 3/1995 | Wilk et al. |
| 5,407,581 A | 4/1995 | Onodera et al. |
| 5,484,442 A | 1/1996 | Melker et al. |
| 5,776,194 A | 7/1998 | Mikol et al. |
| 5,817,052 A | 10/1998 | Johnson et al. |
| 5,858,005 A | 1/1999 | Kriesel |
| 5,868,711 A | 2/1999 | Kramer et al. |
| 5,902,336 A | 5/1999 | Mishkin |
| 5,977,034 A | 11/1999 | Wolfinbarger, Jr. |
| 5,990,382 A | 11/1999 | Fox |
| 6,008,431 A | 12/1999 | Caldarise et al. |
| 6,010,484 A | 1/2000 | McCormick et al. |
| 6,030,358 A | 2/2000 | Odland |
| 6,071,284 A | 6/2000 | Fox |
| 6,210,376 B1 | 4/2001 | Grayson |
| 6,228,088 B1 | 5/2001 | Miller et al. |
| 6,387,098 B1 | 5/2002 | Cole et al. |
| 6,458,117 B1 | 10/2002 | Pollins, Sr. |
| 6,544,266 B1 | 4/2003 | Roger et al. |
| 6,932,827 B2 | 8/2005 | Cole |
| 7,250,055 B1 | 7/2007 | Vanderwalle |
| 7,753,903 B1 | 7/2010 | Burton et al. |
| 7,780,679 B2 | 8/2010 | Bobo, Sr. et al. |
| 7,833,204 B2 | 11/2010 | Picha |
| 8,080,003 B1 | 12/2011 | Burton et al. |
| 8,273,053 B2 | 9/2012 | Saltzstein |
| 8,303,667 B2 | 11/2012 | Younger |
| 8,388,623 B2 | 3/2013 | Browne et al. |
| 8,486,027 B2 | 7/2013 | Findlay et al. |
| 8,715,243 B2 | 5/2014 | Uth et al. |
| 8,801,670 B2 | 8/2014 | Drontle et al. |
| 8,845,573 B2 | 9/2014 | Hausler et al. |
| 8,926,591 B2 | 1/2015 | Schutz et al. |
| 9,050,141 B2 | 6/2015 | Zhang et al. |
| 9,108,018 B2 | 8/2015 | Dickinson et al. |
| 9,149,206 B2 | 10/2015 | Claypool et al. |
| 9,173,679 B2 | 11/2015 | Tzachar et al. |
| 9,198,673 B2 | 12/2015 | Stone |
| 9,216,046 B2 | 12/2015 | Iannotti et al. |
| 2003/0069543 A1 | 4/2003 | Carpenter et al. |
| 2003/0083901 A1 | 5/2003 | Bosch et al. |
| 2003/0208181 A1 | 11/2003 | Geise et al. |
| 2004/0022771 A1 | 2/2004 | Ferree |
| 2006/0015066 A1 | 1/2006 | Turieo et al. |
| 2006/0213836 A1 | 9/2006 | Fissell, IV et al. |
| 2007/0251882 A1 | 11/2007 | Bradwell et al. |
| 2008/0004712 A1 | 1/2008 | Humes et al. |
| 2008/0051696 A1* | 2/2008 | Curtin ................. A61M 1/1696 604/29 |
| 2008/0091270 A1 | 4/2008 | Miller et al. |
| 2008/0215010 A1 | 9/2008 | Silver et al. |
| 2008/0215056 A1 | 9/2008 | Miller et al. |
| 2008/0287859 A1 | 11/2008 | Miller et al. |
| 2009/0118683 A1 | 5/2009 | Hanson et al. |
| 2010/0168691 A1 | 7/2010 | Long et al. |
| 2011/0004163 A1 | 1/2011 | Vaidya |
| 2011/0009915 A1 | 1/2011 | Silver et al. |
| 2011/0077574 A1 | 3/2011 | Sigg et al. |
| 2011/0208319 A1 | 8/2011 | Laster |
| 2012/0095440 A1 | 4/2012 | Islam |
| 2012/0116316 A1 | 5/2012 | Schutz et al. |
| 2013/0041345 A1 | 2/2013 | Kilcoin et al. |
| 2014/0262880 A1 | 9/2014 | Yoon |
| 2014/0276839 A1 | 9/2014 | Forman et al. |
| 2015/0025500 A1 | 1/2015 | Piehl et al. |
| 2015/0314118 A1 | 11/2015 | Kelekis et al. |
| 2016/0015893 A1 | 1/2016 | Hoyt et al. |

FOREIGN PATENT DOCUMENTS

| | | | |
|---|---|---|---|
| DE | 3536178 A1 | 4/1987 | |
| EP | 0476047 B1 | 6/1990 | |
| EP | 0756500 A1 | 2/1997 | |
| EP | 2144662 B1 | 5/2008 | |
| EP | 2349449 A1 | 8/2011 | |
| EP | 2666418 A2 | 11/2013 | |
| EP | 2967592 A1 | 1/2016 | |
| EP | 2967650 A2 | 1/2016 | |
| IL | WO 2010052705 A1 * | 5/2010 | .......... A61M 1/1678 |
| JP | 2001-518934 A | 10/2001 | |
| JP | 2008-068129 A | 3/2008 | |
| JP | 2009503941 A | 1/2009 | |
| SU | 1516121 A1 | 10/1989 | |
| WO | 95/11048 A2 | 4/1995 | |
| WO | 9526763 A1 | 10/1995 | |
| WO | 98/42270 A1 | 10/1998 | |
| WO | 02/096497 A1 | 12/2002 | |
| WO | 2007011983 A1 | 1/2007 | |
| WO | 2008024434 A1 | 2/2008 | |
| WO | 2008/054894 A2 | 5/2008 | |
| WO | 2009148587 A1 | 12/2009 | |
| WO | 2010052705 A1 | 5/2010 | |
| WO | 2013/003885 A2 | 1/2013 | |
| WO | WO 2013/098823 | 7/2013 | |
| WO | 2014142948 A1 | 9/2014 | |
| WO | 2014144262 A1 | 9/2014 | |
| WO | 2014144489 A2 | 9/2014 | |
| WO | 2015123660 A1 | 8/2015 | |

OTHER PUBLICATIONS

International Preliminary Report on Patentability Dated Oct. 30, 2014 From the International Bureau of WIPO Re. Application No. PCTIL2012/050558.

Mar. 16, 2010 International Search Report issued in International Patent Application No. PCT/IL2009/001031.

* cited by examiner

⌀0.20

⌀0.2
⌀0.5

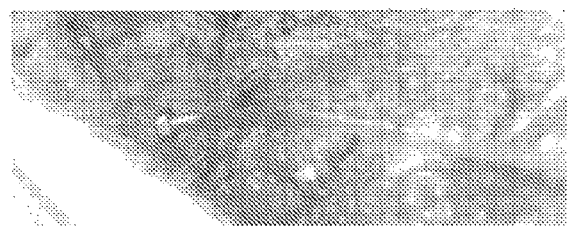
FIG. 12
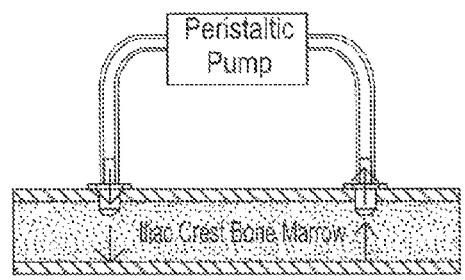
FIG. 13
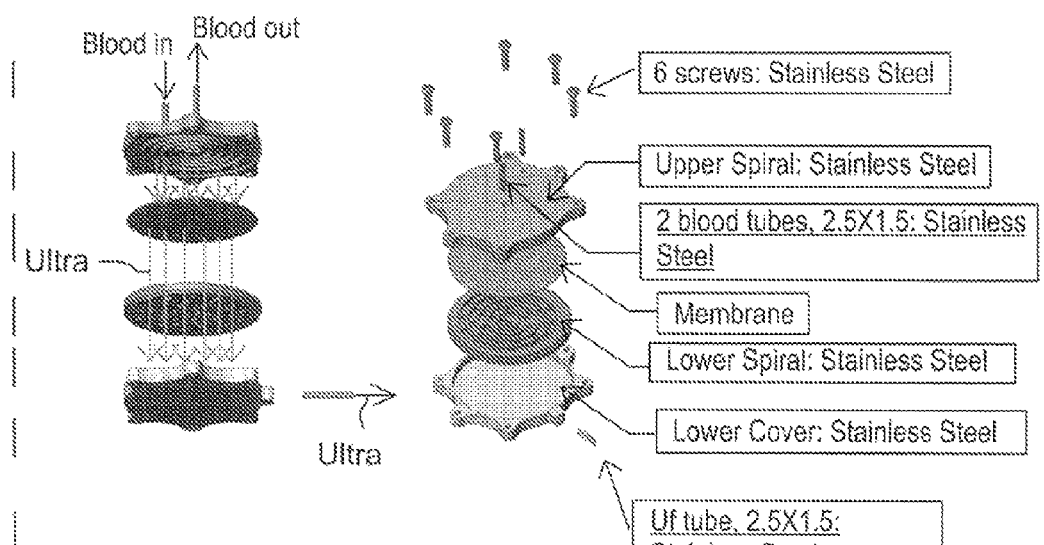
FIG. 14A
FIG. 14B

SYSTEM AND METHOD FOR BLOOD FILTERING AND/OR TREATMENT

RELATED APPLICATIONS

This application is a National Phase of PCT Patent Application No. PCT/IL2012/050558 having International filing date of Dec. 27, 2012, which claims the benefit of priority under 35 USC §119(e) of U.S. Provisional Patent Application No. 61/580,685 filed on Dec. 28, 2011. The contents of the above applications are all incorporated by reference as if fully set forth herein in their entirety.

FIELD AND BACKGROUND OF THE INVENTION

The present invention relates to a system for filtering and/or treating blood and more specifically to a system which is capable of filtering blood from bone marrow and/or altering a property thereof in order to treat a disorder or disease.

Congestive heart failure (CHF) is a condition in which the blood pumping function of the heart is inadequate to meet the needs of body tissue. CHF is one of the most common causes of hospitalization and mortality in Western society.

CHF results from a weakening or stiffening of the heart muscle most commonly caused by myocardial ischemia (due to, for example, myocardial infarction) or cardiomyopathy (e.g. myocarditis, amyloidosis). Such weakening or stiffening leads to reduced cardiac output, an increase in cardiac filling pressures, and fluid accumulation. Reduced cardiac output can lead to diminished kidney function and a result to retention of fluid in body tissue. The lungs and liver may also become congested with fluid, thereby impairing the normal function of these organs. In addition, the intestines may become less efficient in absorbing nutrients and medicines. CHF may result in refractory pulmonary edema which may be treated by IV diuresis or ultrafiltration via hemofiltration or dialysis. Over time, untreated CHF will negatively affect virtually every organ in the body.

End-Stage Renal Disease (ESRD) occurs when the kidneys are no longer able to function at a level that is necessary for day-to-day life, up to the point where kidney function is less than about 10% of a normal, disease-free kidney. The most common cause of ESRD is diabetes. Symptoms of ESRD can include, for example, unintentional weight loss, nausea or vomiting, general ill feeling, fatigue, headache, decreased urine output, easy bruising or bleeding, blood in the vomit or stools, elevated blood urea nitrogen (BUN) levels and decreased creatinine clearance.

Dialysis and/or ultrafiltration are performed on individuals suffering from ESRD or CHF-related fluid overload. The process involves removing waste substances and fluid from the blood that are normally eliminated by the kidneys. Dialysis may also be used in individuals exposed to toxic substances in order to prevent renal failure from occurring.

There are two types of dialysis that may be performed: hemodialysis and peritoneal dialysis.

Hemodialysis involves fluid removal through ultrafiltration, causing free water and some dissolved solutes to move across the membrane along a created pressure gradient. Hemodialysis also utilizes a counter current flow of dialysate which performs adjustments of solutes by creating concentration gradients across the membrane at a maximum and increases the efficiency of the dialysis. The blood is taken by a special type of access, called an arteriovenous (AV) fistula, which is placed surgically, usually in the arm. After access has been established, the blood drains though a large hemodialysis machine which bathes the hemofiltration cartridge in a special dialysate solution that adjusts solute concentration and removes waste substances and fluid. The "clean" blood is then returned to the bloodstream. Hemodialysis is usually performed three times a week with each treatment lasting from 3 to 5 or more hours. Because proper maintenance of hemodialysis equipment (e.g. membranes, pumps) is critical, hemodialysis sessions are often performed at a treatment center. Possible complications of hemodialysis can include muscle cramps and low blood pressure caused by removing too much fluid and/or removing fluid too rapidly. The AV fistula often undergoes thrombosis which limits the use of the fistula and may require surgical interventions for clearing and or replacement of the fistula.

Peritoneal dialysis uses the peritoneal membrane to filter the blood. Peritoneal dialysis is performed by surgically placing a special, soft, hollow tube into the lower abdomen near the navel. A mixture of minerals and sugar dissolved in water, called dialysate solution, is instilled into the peritoneal cavity and is left in the abdomen for a designated period of time in which the dialysate fluid absorbs the waste products, toxins and extra water through the peritoneum membranes. After several hours, the used solution containing the wastes from the blood is drained from the abdomen through the tube. Then the abdomen is refilled with fresh dialysis solution, and the cycle is repeated. The process of draining and refilling is called an exchange. Patients usually undergo four to six exchanges of the dialysis solution per day. An infection of the peritoneum, or peritonitis, is the most common problem of peritoneal dialysis.

Although dialysis is a common procedure it suffers from several disadvantages, including fluids balance impairment, the need of special diet, high blood pressure, psychological problems because of the change in the life style due the need to go to the dialysis treatment several times a week for several hours each time. Due to the increasing numbers of patients requiring dialysis, this introduces a tremendous burden on the healthcare system.

Several attempts have been made to devise systems which overcome at least some of the aforementioned limitations of dialysis devices. U.S. Pat. No. 5,037,385 and Ser. No. 10/922,478 disclose implantable peritoneal dialysis devices. The aforementioned system described includes an implantable peritoneourinary pump system and an implantable dialysate infusion system. When in use, the device has a semi-permeable reservoir implanted in the peritoneal cavity. The reservoir receives blood waste and drains through one or more conduits via a pump to the biological bladder, which is a complicated arrangement.

U.S. Pat. No. 5,902,336 describes another implantable system which employs an ultrafiltration device for removing low to medium molecular weight solutes and fluids from the blood of a patient experiencing renal failure. In this system the fluid flows between the patient's vascular system, through an access to the artery and/or vein, and the patient's bladder or urethra. As such, this system requires surgical attachment of a metal or hard plastic device, to a soft biological tissue (artery or vein), a procedure which often results in undesirable side effects such as vessel shearing/ tearing, clotting, fibrosis, infection and thrombosis.

While reducing the present invention to practice, the present inventors have devised a system which is designed for ultrafiltration and/or treatment of bone marrow blood while overcoming limitations of prior art devices.

SUMMARY OF THE INVENTION

According to one aspect of the present invention there is provided a system for filtering blood of a subject comprising: (a) a bone port configured for establishing fluid communication with a bone marrow of the bone; (b) a fluid fractioning device being in fluid communication with the bone port and being capable of selectively fractioning blood flowing out of the bone marrow to thereby retain a fraction of the blood; and (c) a return port being in fluid communication with the fluid fractioning device and being for returning a non-retained fraction of the blood to a circulation of the subject.

According to further features in preferred embodiments of the invention described below, the system further comprises a fluid conduit for routing the fraction of the blood retained by the fluid fractioning device to a bladder, a Genito-Urinary system or a reservoir.

According to still further features in the described preferred embodiments the system further comprises a device for increasing a blood pressure gradient across the bone port.

According to still further features in the described preferred embodiments the system further comprises a device for increasing a blood pressure gradient across the fluid fractioning device.

According to still further features in the described preferred embodiments the bone port includes at least one elongated cylinder having a central bore.

According to still further features in the described preferred embodiments the fluid fractioning device includes at least one filter.

According to still further features in the described preferred embodiments the filter is impermeable to molecules above a predetermined size and permeable to water and solutes of the blood.

According to still further features in the described preferred embodiments the molecules are 10-500 kDa.

According to still further features in the described preferred embodiments the device is a pump.

According to still further features in the described preferred embodiments the pump is a peristaltic pump.

According to still further features in the described preferred embodiments the system further comprises a mechanism for minimizing clogging of the filter.

According to still further features in the described preferred embodiments the mechanism is configured for creating an electrical field at or near the filter.

According to still further features in the described preferred embodiments the electrical field is an alternating current (AC) field.

According to still further features in the described preferred embodiments the mechanism for minimizing clogging is a blowback mechanism.

According to still further features in the described preferred embodiments (c) is effected by returning the non-retained fraction of the blood to the bone marrow of the bone.

According to another aspect of the present invention there is provided a method of filtering blood of a subject comprising: (a) communicating blood from a bone marrow of a bone of the subject to a fluid fractioning device capable of selectively fractioning blood flowing out of the bone marrow to thereby retain a fraction of the blood; and (b) returning a non-retained fraction of the blood to circulation of the subject thereby filtering blood thereof.

According to still further features in the described preferred embodiments the fraction of the blood includes water and solutes.

According to still further features in the described preferred embodiments (a) is effected by implanting a port in a bone of the subject, the port being in fluid communication with the fluid fractioning device.

According to still further features in the described preferred embodiments the fluid fractioning device is implanted in soft tissue of a body of the subject.

According to still further features in the described preferred embodiments the fraction of the blood retained by the fluid fractioning device is routed to a bladder, a Genito-Urinary system or a reservoir via a fluid conduit positioned between the fluid fractioning device and the bladder, the Genito-Urinary system or the reservoir.

According to still further features in the described preferred embodiments the reservoir is a bag disposed outside the body of the subject.

According to still further features in the described preferred embodiments the fluid fractioning device and reservoir are placed outside the body of the subject According to still further features in the described preferred embodiments the bone marrow is iliac bone marrow.

According to still further features in the described preferred embodiments the subject suffers from chronic kidney disease (CKD) and/or renal failure.

According to still further features in the described preferred embodiments the subject suffers from congestive heart failure.

According to yet another aspect of the present invention there is provided a system for treating blood of a subject comprising: (a) a bone port configured for establishing fluid communication with a bone marrow of the bone; (b) a blood treatment device being in fluid communication with the bone port and being for modifying a property of blood flowing therethrough; and (c) a return port being in fluid communication with the blood treatment device and being for returning the blood to a circulation of the subject.

According to still further features in the described preferred embodiments the blood treatment device includes cells or molecules capable of treatment of hepatic failure, synthesis of insulin, or synthesis of EPO or any other therapeutic protein.

According to still further features in the described preferred embodiments the cells or molecules are encapsulated by a semi-permeable barrier.

According to still further features in the described preferred embodiments the cells are selected from the group consisting of hepatocytes, endothelial cells, renal tubular cells, renal glomerular cells, pancreatic beta cells, neural cells, endothelial cells, fibroblasts.

According to still further features in the described preferred embodiments (c) is effected by returning the blood to the bone marrow of the bone.

The present invention successfully addresses the shortcomings of the presently known configurations by providing a blood fractioning and treatment system capable of filtering or treating blood flowing through the bone marrow. The benefits of the bone marrow filtering include robust blood flow and pressure, a solid organ for the fixation of devices, and prevention of systemic emboli.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 12 illustrates blood flow out of the out port of the screw port.

FIG. 13 schematically illustrates the port-to-port mini circulatory system of the present invention which was tested in a pig model.

FIGS. 14A-B schematically illustrates a membrane filter assembly utilizable with the present invention.

DESCRIPTION OF THE PREFERRED EMBODIMENTS

Figure 1:
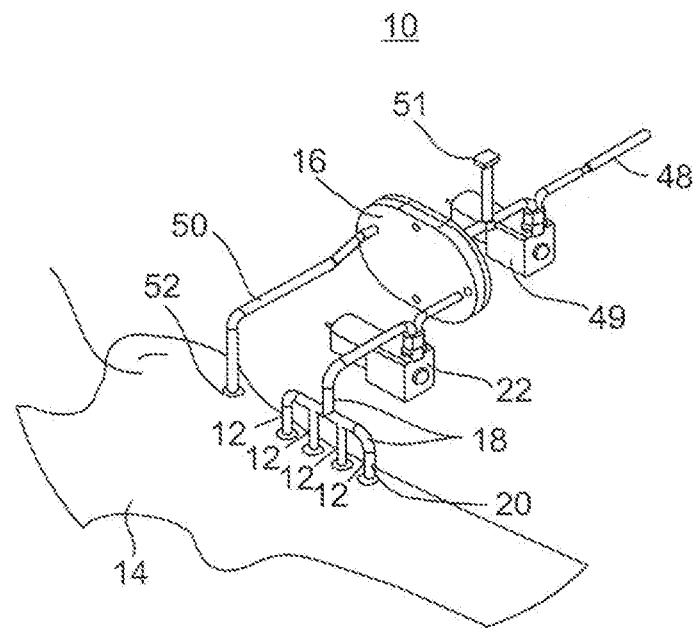
FIG. 1 schematically illustrates one embodiment of the present system.

The present invention is of a system which can be used to filter and/or treat blood flowing through a bone marrow. Specifically, the present invention can be used to compensate for, or correct, failed or failing kidney or cardiac functions and/or treat other conditions such as diabetes, hepatic disease and failure, neurological disease, hematological, metabolic and respiratory diseases as well as provide for the replenishment of missing biomolecules.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Numerous attempts have been made to devise devices which are free of the limitations of standard hemodialysis and peritoneal dialysis approaches.

Although some of these attempts have produced devices that can be effectively used in dialysis (an external process), non-biological implants which are not limited by clotting, infection, soft tissue damage and necrosis, bleeding, and shearing remain a long felt and unmet need.

PCT publication WO/2010/052705 to the present inventor describes a blood filtering device which is configured for filtering blood flowing through a bone marrow. The device includes a device body which is configured for partial or full implantation within a bone marrow of a subject and a filter for filtering the blood flowing through the bone marrow. The device of WO/2010/052705 filters the blood at the source, i.e. at the site of bone implantation to recover a filtrate which is then communicated to the genitourinary system (e.g. bladder) or outside the body.

The bone marrow is an immuno-privileged site and thus can be utilized for the introduction of materials foreign to the host. Such an example is disclosed in U.S. Pat. No. 6,463,933, describing a method for delivering a biologically active substance including: cells, tissues, nucleic acids, vectors, proteins or pharmaceutical compositions to a mammal, by introducing the substance into the bone or bone marrow.

While reducing the present invention to practice, the present inventor experimented with various filtering configurations in efforts to enhance the rate of filtrate generation from bone marrow blood.

As is further described herein, the present inventor has devised a system in which blood is directed from a bone marrow source to a blood circulation sink (e.g. artery, vein, bone marrow) to create an artificial circulatory loop. The system further includes a blood fractioning device (e.g. filter) for recovering a filtrate from blood flowing through the circulatory loop and/or a treatment device for modifying blood flowing through the artificial circulatory loop.

Thus, according to one aspect of the present invention there is provided a system for fractioning blood of a subject such as a human. The present system can be used for blood filtration and thus can be used to supplement or replace renal functions in CHF and CKD/ESRD.

FIG. 1 illustrates one embodiment of the present system which is referred to herein as system 10.

System 10 includes a bone port 12 which is configured for establishing fluid communication with a bone marrow of a bone 14. Examples of bone 14 include, but are not limited to, the axial skeleton and those bones with hematopoietic function. Suitable bones include, but are not limited to, skull, vertebral bodies, iliac crest, rib, sternum long bones, hip, bones of the lower arm, and bones of the upper arm. Bones adjacent to or positioned above the patient bladder or GU system are preferred.

Any number of bone ports 12 can be used with the present system. Four bone ports 12 are shown in FIG. 1, however, a system 10 utilizing 1, 2, 3, 4, 5, 10, 50 or 100 bone ports 12 is also envisaged herein. Likewise, a system 10 including hundreds of needle-like bone ports 12 that traverse the cortex into the marrow are also envisaged herein. A system 10 configuration utilizing more than one bone port 12 can include an anchoring substrate (e.g. anchoring plate) for collectively anchoring a plurality of bone ports 12 connected to the substrate to bone 14.

Bone port 12 is configured as a hollow cylinder fabricated from biocompatible materials such as, for example, titanium, Nitinol, stainless steel, tantalum, SS 316L, Bio Dur 108 Alloy (Nickel free stainless alloy) or any other bone inert/integrative material. Bone port 12 can also be fabricated from a polymer such as Polypropylene, PTFE, ePTFE, PEEK, Nylon, polyether-block co-polyamide polymers, polyurethanes such as aliphatic polyether polyurethanes, PVC, PAN, PS, polyethersulfone, polyethylene, polymethylmethacrylate (PMMA), polyhydroxylmethylmethacrylate (PHMMA), ceramics and the like.

Bone port 12 can be attached to a silicone or polymeric, (Gore-Tex™, PTFE, Polyurethane, Polyethylene, Polypropylene) conduit as is further described below.

Bone port 12 has a length, an outer diameter (OD) and an internal diameter (ID) suitable for establishing fluid communication between the bone marrow and an area outside the bone. Exemplary dimensions of bone port 12 can be OD of 1-10 mm, and ID of 0.2-8 mm. The bone port may have holes to enable blood and bone marrow to get into the port (e.g. hole diameter of 0.2-1.0 mm).

Bone port 12 can be attached to, or implanted within bone 14 via use of bone anchors, screw threads, staples, pins, glue and like. An array of bone ports 12 can also be used. Bone port 12 need not be fully implanted within the marrow region as long as fluid communication is established between marrow blood and a fluid opening at the top of bone port 12. Thus, partial implantation in which one end (distal) of bone port 12 resides within the marrow region and another end (proximal) resides outside the bone is also envisaged by the present inventor. Bone port 12 enables flow both from the bone and to the bone which allows for increased blood flow into the lumen of bone port 12. In that respect, the internal lumen of bone port 12 is configured with a surface which is smooth and highly polished (e.g. N4—average surface roughness 0.2 μm). The internal lumen may include structures for promoting cell attachment and growth (e.g. titanium beads or grooves/indentations within the internal surface). Such structures can be used to direct growth of cells and create compartments within the lumen which are at least partially surrounded by vascularized tissue.

The lumen can alternatively or additionally be coated with anti-fibrotic and/or anti-thrombotic substances such as rapamycin, sirolimus and the like, and/or with PEG polymers, surfactants, neutral polymers (e.g. poly(2-hydroxyethyl methacrylate), polyacrilimide, anionic polymers, phosphoryl choline polymers, gas discharge deposited coatings, self-assembly n-alkyl molecules with oligo-PEG head groups, self-assembly n-alkyl molecules with other polar head groups, natural Hydrophilic Surfaces (e.g. albumin, casein), polysaccharides (e.g. hyaluronic acid, heparin), liposaccharides, phospholipid bilayers or glycoproteins. Such coatings can also be used throughout bone port 12 and the remainder of the device when desirable.

Bone port(s) 12 is fluidly connected to a fluid fractioning device 16 via one or more fluid conduits 18. Fluid conduits 18 (as well as conduits 20, 48, 50 described below) can be fabricated from a polymer (e.g. silicone), a metal (e.g. stainless steel or titanium), Gore-Tex™ (PTFE) or combinations thereof. Conduits 18 are preferably elastic and designed to withstand an inner pressure of about 500 mmHg. In addition conduits 18 are designed to minimize or avoid kinking or alternatively include a bend-limiting element to avoid kinks. Conduits 18 preferably have an ID of 1-4 mm and an OD of 1.5-8.

In the configuration shown in FIG. 1, four bone ports 12 are connected to a single fluid conduit 18 via a manifold connected to four fluid outlets 20 (a four into one configuration).

In order to enhance blood flow from the bone marrow and into fluid conduit 18, system 10 preferably includes a device 22 for increasing a blood pressure gradient across bone port 12 (i.e. between the bone marrow and fluid conduit 18). Device 22 can be a pump 22 which creates a pressure differential of, for example, 50-500 mmHg. Pump 22 is preferably a Peristaltic pump (e.g. Thomas SR10\30 or Welco wpm 1). A peristaltic pump is preferred since it provides several advantages: a) size and simplicity; b) the pump mechanism surrounds and squeezes the elastic tubing and enables pressure buildup with no additional mechanical parts within the tube, thus no direct contact of additional components or materials is made negating the risk of contamination; c) minimal components, no valves are required; d) small size, low energy; e) no energy required to maintain a holding position in either +/−pressure state; f) bi-directional flow ability; g) no flow disturbance; h) easy to sterilize and clean; i) can handle viscous and shear-sensitive fluids and prevent backflow and syphoning without use of valves. Pump 22 can also be a pulsating pump such as Diaphragm pump (e.g. Schwarzer Precision model 270-EC-DB-L www-dotschwarzerdotcom/pages_en/produktdotphp?id=95).

Pump 22 can also be a miniature impeller pump positioned within conduit 18. Such a pump can have a wide inlet and a narrow outlet configuration that can increase blood flow therethrough thereby enhancing blood flow from the bone marrow. Such a pump configuration can be fabricated from zirconium-niobium alloy and titanium-zirconium-niobium alloy as well as carbon coating techniques.

Blood flow from the bone marrow can also be enhanced by introducing ridges into the inner surface of conduits 18.

As is mentioned hereinabove, fluid conduit 18 routes blood from the bone marrow to a blood fractioning device 16.

Device 16 can be any device capable of fractioning blood flowing therethrough and retaining a fraction which is substantially devoid of cells and varying levels of proteins and ions depending on the anticipated usage of system 10 (e.g. serum with or without protein depending on filtering). Device 16 can fraction blood via centrifugation (vortex tube), polarization or filtration.

Device 16 can fractionate the blood using a single fractionation step or via several steps in which each step fractionates the filtrate obtained from the previous step.

Figure 3:
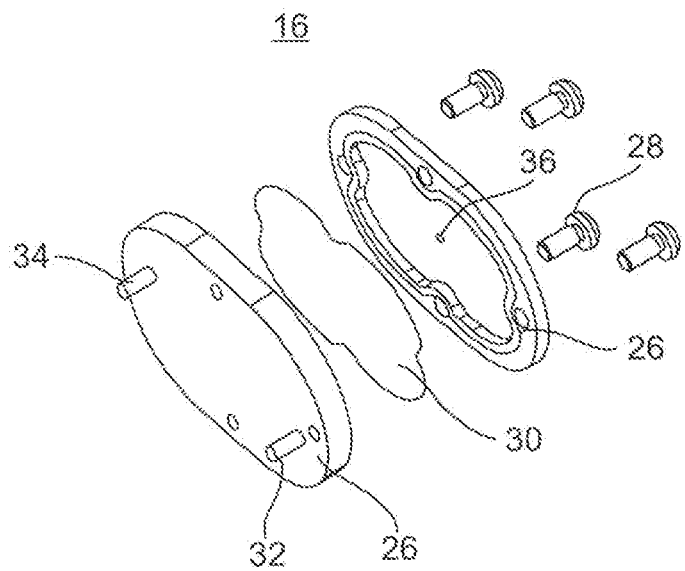
FIG. 3 schematically illustrates an exploded view of a blood fractioning device having a single filter assembly.

FIG. 3 illustrates one configuration of device 16. Device 16 includes a housing 26 (two halves fastened with screws 28, welded or glued) surrounding a filter 30. Housing 26 is fitted with input and output ports 32 and 34 (respectively) which conduct blood over filter 30 and an filtrate port 36 which conducts the fraction retained by device 16 to a target collection reservoir or vessel (further described hereinbelow).

Figure 15:
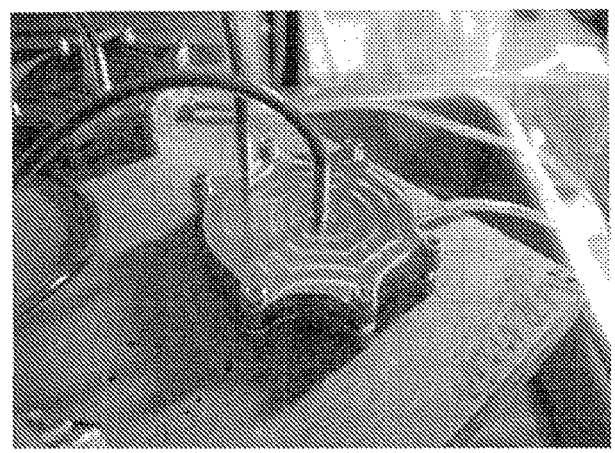
FIG. 15 illustrates a prototype membrane filter assembly constructed according to the teachings of the present invention.

Housing 26 may be configured (internally) with channels/grooves that direct flow across the membrane (e.g. a housing with an internal spiral channel which directs fluid flow or any other configuration that can increase flow rate of blood past the filtration membrane). Another embodiment of device 16 is shown in FIGS. 14*a-b* and 15.

Filter 30 is permeable to water and solutes and impermeable to blood cells and biomolecules above a predetermined size (e.g. proteins, complex carbohydrates etc). Filter 30 preferably has a cutoff size selected from a range of 5-500 kDa. As such, filter 30 can restrict molecules above 5 kDa, 10 kDa, 15 kDa, 20 kDa, 25 kDa, 30 kDa, 35 kDa, 40 kDa, 45 kDa or 50 kDa from passing through the filter and being routed to the collection reservoir or vessel. Filter 30 can also include a combination of filters with different cutoffs. Filter 30 is preferably configured to withstand pressures of at least 400-500 mmHg or more (up to 1 ATM) without tearing and has a minimum surface area of 5 mm2, although larger surface areas in the range of 700 $cm^2$ are preferred. The surface area of filter 30 can be increased by rolling filter 30 into rods or by folding it into a three dimensional structure, or other techniques such as utilized in dialysis equipment, radiators, coolant systems or alike.

Filter 30 can be composed of any material suitable for such purposes, examples include metals, alloys, polymers, ceramics, biological material or combinations thereof.

Metal or alloy filters can be composed of stainless steel, nickel titanium alloys, cobalt-chrome alloys, molybdenum alloys, tungsten-rhenium alloys, liquid metal or any combination thereof.

Polymeric filters can be composed of polyacrylonitrile, polysulfone, polyethersulfone, polyethylene, polymethylmethacrylate, polytetrafluoroethylene (PTFE), polyester, polypropylene, polyether ether ketone, Nylon, silicone, polyether-block co-polyamide polymers, polyurethanes such as aliphatic polyether polyurethanes, polyvinyl chloride, thermoplastic, fluorinated ethylene propylene, cellulose, collagen, silicone or any combination thereof.

Filter 30 can be of a woven or non-woven configuration. Approaches for producing woven or non-woven filters are well known in the art.

Figure 4:
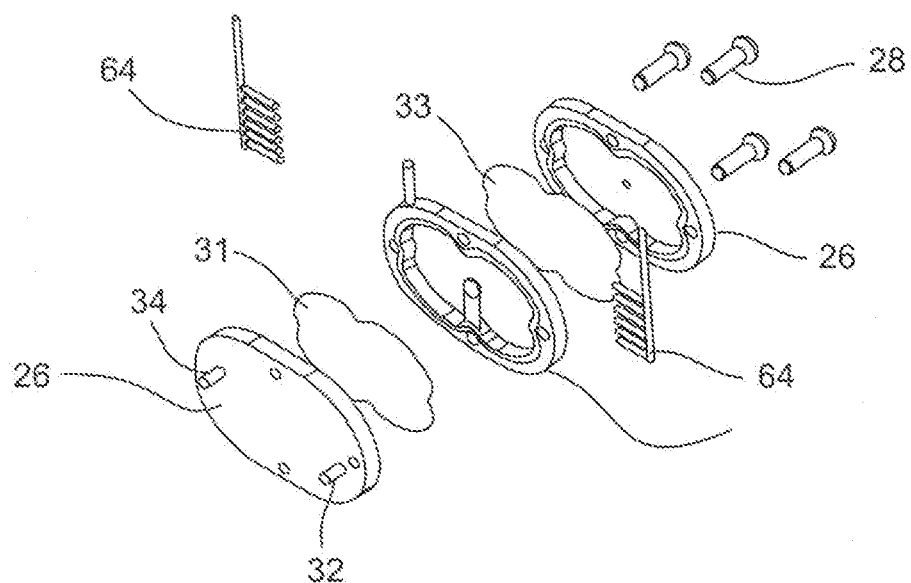
FIG. 4 schematically illustrates an exploded view of a blood fractioning device having a double filter assembly.

Any number of filters can be used in device 16. FIG. 4 illustrates a two filter configuration of device 16 in which the blood is filtered in a stepwise manner through a first filter 31 removing cells and then through a second filter 33 removing large biomolecules.

Two stage (also referred to herein as step-down) filtering is utilized to perform coarse filtration followed by fine filtration. Coarse filtration is effected using a 1 micron filter, fine filtration is effected using a 10-500 kD MWCO filter. This enables efficient energy usage since in the case of blood which includes solutes as well as cells it is easier to perform coarse filtration to remove most of the cells followed by a fine filtration of serum rather than whole blood.

Step-down filtering also enables collection of a serum like fluid (following coarse filtration) that can then be treated or ionically adjusted (e.g. solutes) in order to augment fluid reduction and adjust the patient's pH and ion concentration. Following such treatment, the coarse filtrate can be returned to the circulation as described herein.

Device 16 can be surgically implanted between the muscle and skin and connected to the ports as described above. Due to its proximity to the skin, device 16 can be periodically accessed (injection port) in order to inject various substances to clear filter 30 or to inject dialysate type solutions which may also enable dialysis potentially via sorbent dialysis systems such as Zeolite, conventional divalent exchanger, zirconium silicate or and other cation exchange system. The site of the filtration unit under the skin would also allow for inductive charging through the skin.

In order to reduce clogging (fouling) of filter 30, device 16 preferably includes a mechanism for clearing the surface of the filter or preventing fouling thereof. Such a mechanism can include a pump, a scraper/scrubber, an ultrasonic emitter and the like or a mechanism for creating an electrical or magnetic charge/polarization at or near filter 30.

Figure 6:
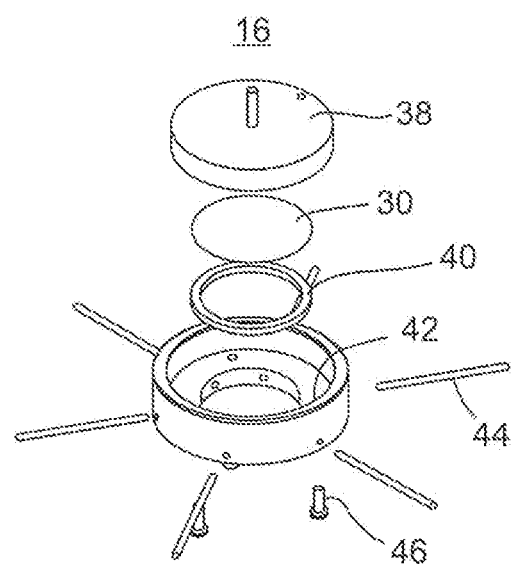
FIG. 6 schematically illustrates an exploded view of an electrically charged/polarized blood fractioning device constructed in accordance with the teachings of the present invention.
Figure 7A:
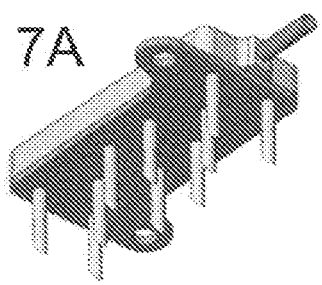
FIGS. 7A-D schematically illustrate a prototype needle array port used in the pig study.
Figure 7B:
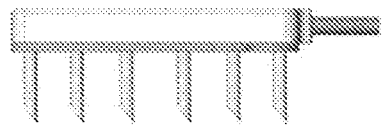
Figure 7C:
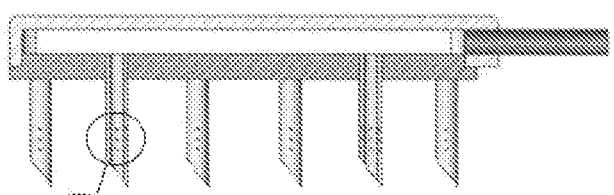
Figure 7D:
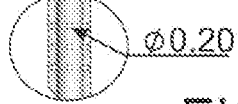

FIG. 6 illustrates one configuration of a device 16 which includes a mechanism for creating an alternating electrical charge/polarization at filter 30. The Examples section which follows describes use of such a filter.

Device 16 includes a filter housing 38 which functions as a cathode, a filter 30, a sealing sleeve 40, an electrically insulated cover 42, electrically conductive rods 44 (preferably gold or alike plated) and assembly screws 46.

By polarizing the filtering surface of filter 30, charged or polarized blood constituents (e.g. glycoproteins) can be rejected or attracted in accordance with their electrical charge/polarization, thus enabling sorting of molecules and minimization of membrane fowling. AC polarization is more effective than DC polarization since proteins generally have a negative charge, while many solutes can have either a positive or negative charge. If only a negative charge is applied to the filter surface, the proteins will be repelled but cations such as Na++ or K++ etc will be attracted to the membrane and cause fouling. By using AC current, all the molecules are alternately attracted and repelled. The net effect of this attraction/repulsion of all molecules can keep the membrane clean and/or be used to clean the membrane.

Thus, system 10 routes blood from bone marrow through, or over, one or more filters (or alternative fractioning devices) to retain a filtrate that is largely composed of water and solutes. The water and solutes are then routed via fluid conduit 48 from a filtrate port 36 of device 16 to the Genito-Urinary (GU) system, bladder, or a reservoir disposed within or outside the body (e.g. collection bag). Conduit 48 can include a second pump 49 for increasing the pressure gradient between device 16 and the target collection reservoir/tissue; pump 49 can be similar or identical to pump 22. The flow rate generated by pump 22 should preferably be much higher than the flow rate of pump 49 (The blood-filter contact time should remain low and flow velocity over the membrane surface should be high to diminish the risk of membrane fouling). Pump 49 can be used to generate a negative pressure while maintaining a relatively low flow rate through device 16. Pump 49 can also be used to generate backflow of fluid to clear filter 30. Conduit 48 can have a diameter ranging between about 1 to about 30 mm, preferably about 4 to about 10 mm and a length of about 50 to about 400 mm or preferably about 100 to about 200 mm.

The non-retained fraction (cells large biomolecules, water and solutes) can be routed back to circulation (preferably bone marrow or a blood vessel such as a vein artery).

The non-retained portion of the blood is routed back to circulation via fluid conduit 50 (diameter of 2-10 mm and a length of 15-100 mm) which is connected to a bone-anchored return port(s) 52 or a blood vessel. When routed back to a bone (e.g. bone 14), return port 52 is preferably configured for fluid communication with a bone marrow of the bone. As such, return port can be of similar dimensions and materials as bone port 12. When routed back to a blood vessel, conduit 50 is connected to a return port which is configured as a standard synthetic graft to vessel anastomoses.

It will be appreciated that in the case of a system 10 which includes return ports 52 connected to bone marrow, the system can reverse flow by changing the pressure gradient, such that blood from the bone marrow will flow from the bone marrow through port 12 to the filter and return to the bone through port(s) 52, or that blood from the bone marrow will flow through ports 52 and return to the bone marrow through ports 12). Such reversal of flow can be used to enable cleaning of the ports.

System 10 further includes pressure sensor 51 for monitoring the pressure at the receiving side of the membrane. The pressure data received from pressure sensor 51 enables system 10 to maintain the required pressure gradient by selectively operating pump 22 and/or 49.

Figure 2:
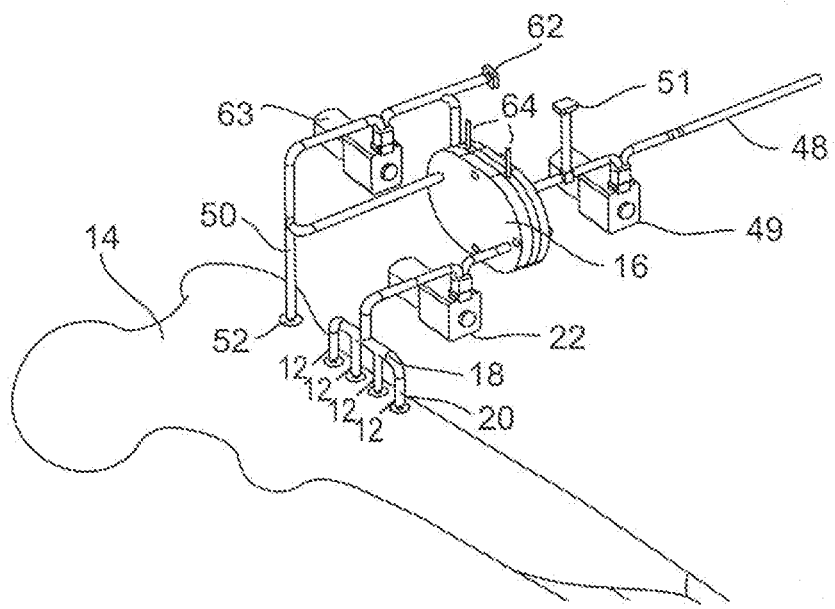
FIG. 2 schematically illustrates another embodiment of the present system.

FIG. 2 illustrates another configuration of system 10 which utilizes a two stage filter, coarse filtering such as with a 1 micron pore size 0.2-4 micron followed by fine filtering 10-500 kD MWCO filter. Pump 22 creates constant blood flow across the first stage coarse filter 31. Pump 63 vacates the first stage filtered blood slowly back to the bone marrow while the pressure between the membranes is monitored by sensor 62. The filtrate of filter 31 flows across a fine filter 33 to generate a second filtrate which is evacuated from the body as described above. The primary filtrate can be then treated to preferentially and selectively remove additional solute such as potassium before allowing the primary filtrate to undergo further filtration which will then be directed to the GU system. While the proteinaceous primary filtrate will then shunt back into the circulatory system via the bone marrow or vessel. Such a two stage filtering approach is advantageous in that it may increase the life cycle of the filtering membranes and enable more thorough filtering. This configuration may also allow for increased treatment or modification of filtered serum such as selective and preferential excretion of solute, self generation of dialysate and acid/base adjustment.

The membranes may also contain protein secreting cells that are protected from the immune system and can be used to add proteins such as insulin, glucocerebrosidase, Factor VIII or other beneficial biomolecule. Renal tubular cells or hepatic cells that can be used for solute adjustment and detoxification of blood or serum can also be used with the present invention. Device 16 containing hollow fibers may be open to air in order to assist respiratory function. Pump 49 creates a pressure gradient across fine filter 33, this pressure gradient is monitored by sensor 51 and adjusted to enhance ultra filtrate flow through filter 33 and into tube 48.

System 10 can further include a sensor or sensors (not shown) for sensing a concentrate of an analyte (e.g. glucose, BUN, Cr, Na, K, Cl, $HCO_3$ pH etc) or for identifying blood parameters such as coagulation (e.g. blood viscosity and PT/PTT coagulation using a MEMs sensor such as that described in US20110302996) in the filtered bone marrow blood or in the recovered filtrate. The sensor(s) can be positioned, for example, within input port 32 or filtrate port 36 or along the conduits leading thereto. The sensor can utilize an amperometric enzyme probe, an optical probe or any other known probe suitable for measuring and generating an electrical sensor signal in response to analyte concentrations or to the parameters measured.

The system of present invention can also include a wireless communication unit (which can be positioned within bone port 12 or device 16) for communicating a filtration rate and optionally analyte sensor data to an extracorporeal control unit. The control unit can be used to control system operations such as filter defouling, pressure gradient (in the case of system 10 which includes pump 22 and/or 49) according to data communicated from sensors positioned in or on bone port 12, device 16 or conduits 18/48. Wireless communication and operation can be effected using RF, magnetic or ultrasonic communication approaches which are well known to the ordinary skilled artisan.

The present system can operate without any control over functions, or it can operate as a closed or an open loop system. In the closed loop configuration, the present system can incorporate a feedback loop which adjusts the pressure gradient according to the amount of water and solutes removed from the blood. The amounts of water removed can be measured via a sensor positioned within device 16 conduit 18/48 or the collection bag. Adjustment of the pressure gradient across filter 30 can then be controlled via a microprocessor positioned within device 16 and being in control of pump 22/49. In an open loop configuration, fluid flow sensor data can be sent to an extracorporeal processing and control unit. The processing unit can be first calibrated by a physician based on initial filtration rates. The processing unit can be recalibrated periodically (e.g. once or several times a year) if need be.

The present system may also include an indicator mechanism for alerting the subject or treating physician of filter 30 clogging or failure. Filter 30 clogging can be detected via an increase in pump 22/49 backpressure. Such an increase can be relayed wirelessly to an extracorporeal warning/control unit. Filter 30 failure can be detected by incorporating marker dyes into filter 30. Filter 30 breakdown would result in appearance of such a dye in the urine.

Although use of filter 30 clearing mechanisms such as those described hereinabove will ensure long duty cycle, use over extended periods of time (e.g. months, years) might necessitate filter replacement. In order to address such need, the present system preferable carries filter 30 or device 16 in a replaceable cartridge which can be exchanged via a minimally invasive procedure.

The present system provides several advantages when utilized in filtration of blood:
(i) minimizes contact of foreign body with bone marrow;
(ii) allows for increased surface area of filter with minimal drilling into the bone marrow, minimizing damage to the bone;
(iii) increasing flow past filter thereby increasing efficiency of filtration and reducing membrane fouling;
(iv) step down filtration may set up the basis for more advanced solute and filtration adjustments. i.e a fully functional kidney;
(v) mini-circulatory loop (from bone port to circulation) facilitates filter replacement;
(vi) the risk of clots being propagated systemically is significantly mitigated by re-introduction of retained fraction into bone marrow which would filter out any unwanted emboli prior to entering the general circulation.
(vii) flow past membranes or capsules may prevent fibrosis of membranes (hollow fiber or encapsulated) and be used for the immuno-protection of foreign cells;
(viii) fixation of device to bone more stable than blood vessel anastomosis; and
(ix) having an in/out port that can be reversed may ensure free flow of blood within the bone marrow and prevent fibrosis.

Figure 5:
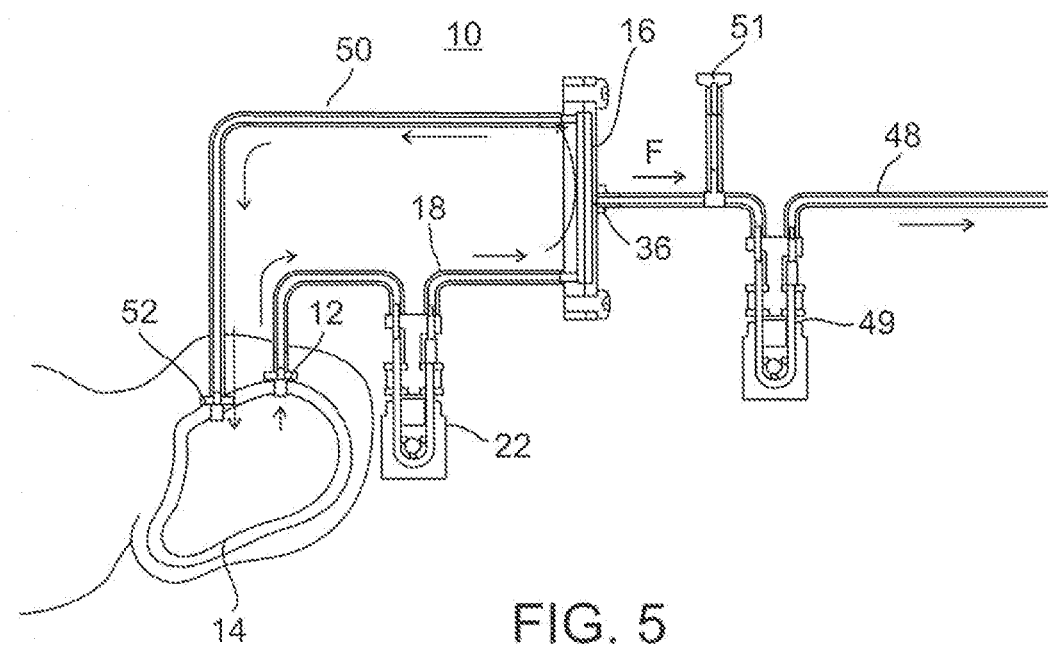
FIG. 5 is a schematic cross sectional view of one embodiment of the present system.

FIG. 5 illustrates the operation of system 10. Blood flowing out of bone marrow through bone port 12 (flow enhanced under the negative pressure applied by pump 22 is routed via conduit 18 into device 16. The blood is fractioned by one or more filter 30 into a filtrate (F) which flows out of port 36 of device 16 (under the negative pressure applied by pump 49). Conduit 48 carries the filtrate out of the body (into a collection bag) or into the GU system. The non-filtered portion of the blood is returned to circulation (e.g. bone marrow) via conduit 50 and return port 52.

As is mentioned hereinabove, system 10 of the present invention is highly suitable for use in treatment of fluid overload due to CKD/ESRD or CHF in the patient.

Given the fact that the flow of blood through the bone marrow can achieve a naturally occurring pressure gradient of 25-40 mmHg. The pump structure can increase the gradient to many hundreds of mm Hg or more (500 mmHg with pump 49) with respect to the collection reservoir or GU system, a minimum of 50 ml of water per 24 hr period can be removed by the present system. Such an amount of water would be sufficient for beneficial clinical effect especially for CHF patients.

Thus, the present invention also provides a method of treating CKD/ESRD or CHF. The method includes implanting within a patient in need the system disclosed herein.

A bone is exposed, and ports 12 and 52 inserted in to the requisite bone via drilling or tapping. The bone plugs or plate with ports are fixated to the bone and then the system components are attached. System components (filter 16, pump 22 and conduits 18) are connected to ports 12 and 52 and fixated to the bone or implanted in a subcutaneous pouch. The egress of filtered fluid is shunted to the GU system. The fluid may also be shunted to a collection device residing outside the body. Device 16 may be fixated to bone, implanted subcutaneously and may be designed as a cartridge that may be easily replaced. Device 16 may also be placed outside the body or provided with access to air.

The present invention can also be used to treat the blood flowing out of the bone marrow.

Thus according to another aspect of the present invention there is provided a system for treating blood of a subject. As used herein, the phrase "treating blood of a subject" refers to altering a property of blood on a physiological (e.g. solute concentration/balance), biochemical (removing or adding specific biomolecules) or cellular (removing or adding specific cell populations) level.

A system for treating blood includes a bone port (identical to bone port 12) which is in fluid communication with a blood treatment device (via a fluid conduit and optionally a pump such as those described for system 10). The blood treatment device is configured for modifying a property of blood flowing therethrough. The treated blood is then returned to circulation (e.g. bone marrow) via a return conduit and port(s) (such as those described for system 10). Thus, the blood treatment device of the present invention includes an artificial circulatory loop such as that described for system 10, but instead of filtering the blood flowing through such loop it treats it.

The blood treatment device can include cells, enzymes or other biologically active entities. The blood may be shunted though or around hollow fibers surrounded by, or containing cells. The cells can be renal tubular cells for treating kidney disease, hepatocytes for treating hepatic failure, beta cells for treating diabetes, nerve cells secreting dopamine for the treatment of Parkinson's or BDNF for the treatment of neurodegenerative disease, fibroblasts to secrete EPO or missing proteins such as Factor VIII or enzymes such as Glucocerebrosidase for Gaucher's disease.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

In Vitro Filtration of Blood Using an AC-Polarized Filter Assembly

The filter assembly described in FIG. 6 was used to filter fresh pig blood.

The testing system included a tank filled with 1 liter of fresh pig blood which is heated to 35-37 C oxygenated and stirred attached via a tube to the filter assembly. A vacuum pump capable of creating a vacuum of (−20)-(−70) mmHg was attached to a collecting tube attached to the filter assembly. Pressure is created within the tank for creating positive pressure of 30 mmHg inside the jar (resulting in a total of 50 mmHg pressure gradient across membrane). The filter cleansing was achieved via AC current applied at 200 Hz 1.5V with a duration of experiment being 8 hours. Filtration flow rate graph is obtained from the system's software and analyzed, the ultrafiltrate was sent for laboratory analysis. The results showed that as compared to straight filtration or as compared to blowback clearing, the AC current ultrafiltration membranes reduced the SD of filtration flow rate by half which indicates significant improvement in the efficiency of the filtration membrane which suggests that the membrane was kept cleaner.

Example 2

Pig Study

Figure 8A:
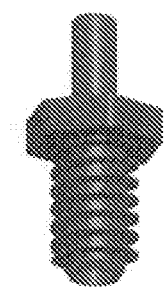
FIGS. 8A-B schematically illustrate a prototype screw port used in the pig study.
Figure 8B:
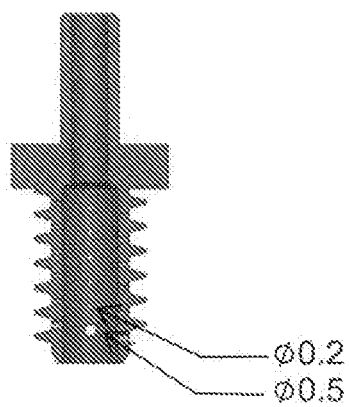

A pig model was utilized to test iliac crest bone marrow blood flow using several combinations of two port configurations, a needle array port (FIGS. 7*a-d*) and a screw port (FIGS. 8*a-b*). Several parameters were tested including dimensions, implantation process and sealing, as well as blood flow rate through the port with and without suction.

Materials and Methods

Needle Array Port

A single 90 kg adult female pig was anesthetized and the iliac crest was exposed. Initially a 20,000 IU dose of Heparin was provided (i.v.) followed by a 12,500 IU dose 2 hours later.

Figure 9A:
FIGS. 9A-B illustrate use of a jig for drilling holes for the needle array port of FIGS. 7A-D.
Figure 9B:
Figure 9B:
Figure 10:
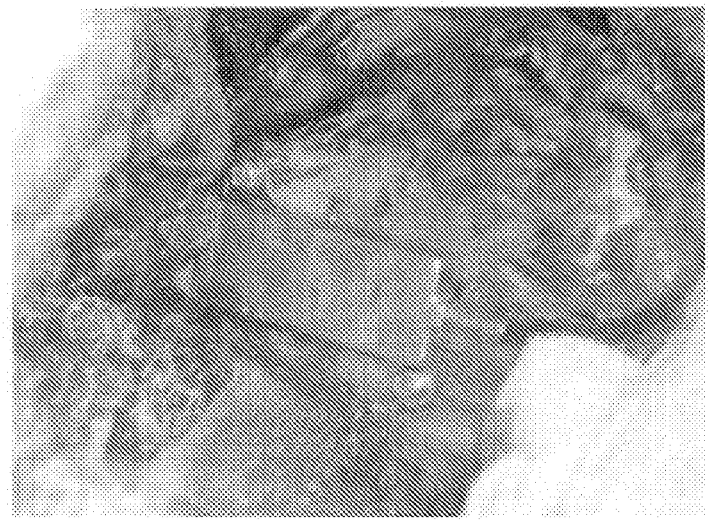
FIG. 10 illustrates the needle array port prototype attached in position over the iliac crest bone.
Figure 11:
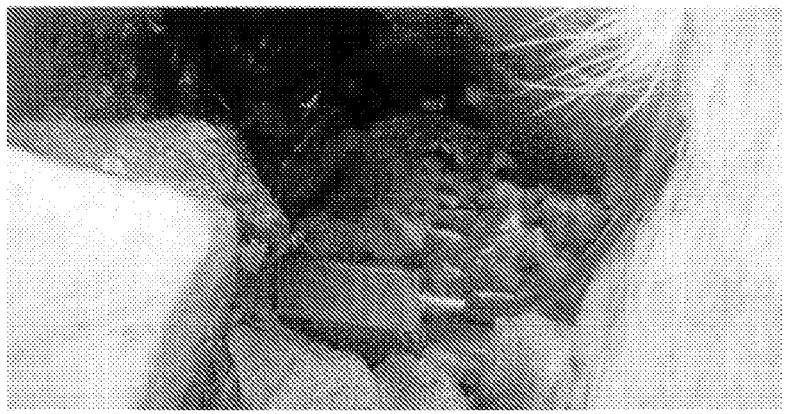
FIG. 11 illustrates blood flow out of the out port of the needle array port.

A jig (FIG. 9*a*) was used to create holes in the iliac crest (FIG. 9*b*) and a needle array including 10 needles, each having a length of 8.5 mm and 0.2 mm holes at the distal portion, was positioned with the needles inserted within the drilled holes (FIG. 10). No leakage of blood out of the needles was observed. The array plate was attached to the iliac crest via two screws. Blood flow through the out port of the array was observed following attachment thereof (FIG. 11). Without applying suction, blood flow through the out port tube was measured using a pressure sensor, measuring tape and a stopwatch.

Screw Port

A hole was drilled in the iliac crest using a 3.5 mm drill bit. The screw port was implanted (FIG. 12) and no leakage of blood out of the port was observed. Without applying suction, blood flow through the out port tube was measured using a pressure sensor, measuring tape and a stopwatch.

An electronic pump unit (Thomas, 12V, Model 20300515), was connected to the out port of the needle array or screw port and suction was applied. Flow rate and pressure were measured by using a test tube and stopwatch or a dedicated software application which controls the pumps, receive readings (inputs) from the sensors (flow rate indication) and from the pressure sensors and store the experiment data.

Implantation of a Second Port

A second port (needle array or Screw type) was implanted as described about 5 cm away from the first implanted port (needle array or screw type), no leakage of blood out of the screw-port was observed. The two screw ports were fluidly connected through a peristaltic pump (FIG. 13) via their out ports in order to assess circulation.

Suction was applied resulting in blood flow from the Iliac crest bone marrow through one port toward the other port and back to the Iliac Crest bone marrow, flow rate and pressure were measured.

Needle Array to Needle Array Circulation

Leakage around the needle holes was observed. Putty soft (Zhermack elite HD+) was used and appropriate sealing was achieved. Suction was applied resulting in blood flow from the Iliac crest bone marrow through one needle array towards the other Needle array and back into the Iliac Crest bone marrow, flow rate and pressure were measured.

Needle Array to Screw Port Circulation

Suction was applied resulting in blood flow from the Iliac crest bone marrow through one needle array towards the screw port and back into the iliac crest bone marrow, flow rate and pressure were measured.

Screw Port to Needle Array Circulation

Suction was applied resulting in blood flow from the Iliac crest bone marrow through the screw port towards the needle array and back into the iliac crest bone marrow, flow rate and pressure were measured.

In all cases, back flow was also measured.

Results

The blood flow results with and without suction are summarized in table 1 below. The pressure measured for natural blood flow in bone marrow (without suction) is 30-32 mmHg.

TABLE 1

| Blood flow through | Flow rate [mm3/hour] | Flow rate [ml/hour] |
| --- | --- | --- |
| Needle structure without suction (natural flow) | 18,095.5 | 18.0955 |
| Screw-port without suction (natural flow) | 3,820.2 | 3.8202 |
| Needle structure with suction | 22,784.8 | 22.7848 |
| Screw-port with suction | 17,734 | 17.734 |
| Circulation: Needle structure to Needle structure with suction | 19,200 | 19.2 |
| Circulation: Needle structure to screw-port with suction | 19,200 | 19.2 |
| Circulation: screw-port to Needle structure with suction | 19,200 | 19.2 |
| Circulation: Needle structure to Needle structure with suction using 2 pumps | 38,460 | 38.46 |

Summary of Findings

Implantation of both screw and needle array-type ports was fast and easy. The blood flow rate through the needle structure was much higher than through the screw port. In both case, excellent bone marrow-to-bone marrow blood circulation was observed. A stronger pump (with a higher flow rate) can be used to increase the natural flow rate in cases where higher flow rates are desired. The pump system was effective at restoring full flow rates by blowing back obstructions that decreased flow.

Example 3

Filter Membrane Study

A filter assembly (FIG. 15) was constructed using the components illustrated in FIG. 14b. A Novasep Prostream 100 kDa membrane (effective filtration—1090 mm$^2$) was clamped between two metal plates each having a spiral slot (with 364 mm total spiral length). As schematically shown in FIG. 14a, blood enters the upper metal plate through an inflow port and flows within the spiral slot over the membrane. The Ultra filtrate flows down towards a lower metal cover to be pumped out of the filter structure through a metal tube. The retained fraction is ejected out of the filter assembly from a metal tube positioned at the end of the spiral path.

Blood was pumped from a jar into the filter structure using a peristaltic pump (Thomas, 12V, Model 20300515). The blood flowed over the membrane within a spiral slot and back to the jar. Using a second peristaltic pump, the ultrafiltrate, which accumulated beneath the membrane, was pumped out from the filter structure into a sterile test tube. The test tube was placed on an electronic scale, which was connected to a computer and a graph representing ultrafiltrate as a function of time was generated.

Figure 16:
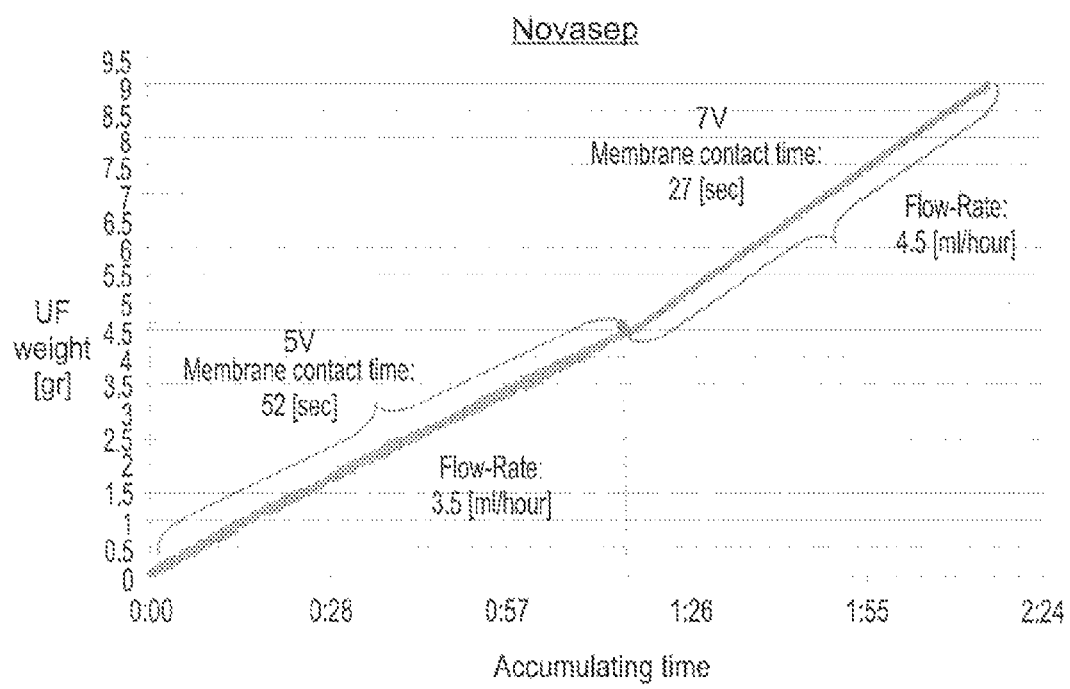
FIG. 16 is a graph illustrating the flow rate and ultrafiltrate collection through a filter assembly including a Novasep membrane.

FIG. 16 illustrates the graph obtained from Novasep Prostream membrane. The graph has two regions: input voltage of 5 [V] and input voltage of 7 [V]. As expected, the flow rate corresponding to an input voltage of 7 [V] is higher than the flow rate for an input voltage of 5 [V]. At input voltage of 7 [V], an average of 4.5 [ml/hour] was obtained.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for filtering blood of a subject, the system comprising:
   a bone port fixable to a bone and configured for establishing fluid communication with a bone marrow of said bone;
   a fluid fractioning device capable of selectively fractioning blood flowing out of said bone marrow to thereby retain a fraction of said blood;
   a first fluid conduit connectable between said bone port and said fluid fractioning device, and configured to establish fluid communication therebetween;
   a return port configured for returning a non-retained fraction of said blood to a circulation of the subject; and
   a second fluid conduit connectable between said fluid fractioning device and said return port, and configured to establish fluid communication therebetween.

2. The system of claim 1, further comprising a third fluid conduit connectable between said fluid fractioning device and a bladder, a Genitourinary system, or a reservoir, and configured for routing said fraction of said blood retained by said fluid fractioning device to said bladder, said Genitourinary system, or said reservoir.

3. The system of claim 2, further comprising a device for increasing a blood pressure gradient across said fluid fractioning device.

4. The system of claim 3, wherein said device is a pump.

5. The system of claim 4, wherein said pump is a peristaltic pump.

6. The system of claim 1, further comprising a device for increasing a blood pressure gradient across said bone port.

7. The system of claim 1, wherein said fluid fractioning device includes at least one filter.

8. The system of claim 7, wherein said filter is impermeable to molecules above a predetermined size and permeable to water and solutes of said blood.

9. The system of claim 8, wherein said molecules are 10-500 kDa.

10. The system of claim 7, further comprising a mechanism for minimizing clogging of said filter.

11. The system of claim 10, wherein said mechanism is configured for creating an electrical field at or near said filter.

12. The system of claim 11, wherein said electrical field is an alternating current (AC) field.

13. The system of claim 1, wherein said bone port includes at least one elongated cylinder having a central bore.

14. The system of claim 1, wherein said return port is configured for returning said non-retained fraction of said blood to said bone marrow of said bone.

15. The system of claim 1, wherein said return port is fixatable to said bone or to another bone.

16. The system of claim 1, wherein said return port is configured to establish direct fluid communication with a blood vessel.

17. The system of claim 1, configured to allow flow reversibility between said bone port and said return port.

18. The system of claim 1, wherein said fluid fractioning device is configured for implantation between muscle and skin of the subject.

19. A method of filtering blood of a subject, the method comprising:
   communicating blood from a bone marrow of a bone of the subject to a fluid fractioning device capable of selectively fractioning blood flowing out of said bone marrow to thereby retain a fraction of said blood, said communication is effected via a bone port fixable to said bone, and, via a first fluid conduit connectable between said bone port and said fluid fractioning device and configured to establish fluid communication therebetween; and
   returning a non-retained fraction of said blood to circulation of the subject, said returning is effected via a return port, and, via a second fluid conduit connectable between said fluid fractionating device and said return port and configured to establish fluid communication therebetween, thereby filtering blood thereof.

20. The method of claim 19, wherein said fraction of said blood includes water and solutes.

21. The method of claim 19, wherein said communicating is effected by implanting said bone port in said bone of the subject.

22. The method of claim 19, wherein said fluid fractioning device is implanted in soft tissue of a body of the subject.

23. The method of claim 19, wherein said fraction of said blood retained by said fluid fractioning device is routed to a bladder, a Genito-Urinary system or a reservoir via a fluid conduit positioned between said fluid fractioning device and said bladder, said Genito-Urinary system or said reservoir.

24. The method of claim 19, wherein the subject suffers from CKD, renal failure or congestive heart failure.

* * * * *